United States Patent [19]

Nagata

[11] Patent Number: 5,005,496
[45] Date of Patent: Apr. 9, 1991

[54] METHOD FOR DISPOSAL OF MEDICAL WASTE MATERIALS

[75] Inventor: Hirofumi Nagata, Onoda, Japan

[73] Assignee: Kyoei Steel Ltd., Osaka, Japan

[21] Appl. No.: 376,092

[22] Filed: Jul. 6, 1989

[30] Foreign Application Priority Data

| Jul. 7, 1988 | [JP] | Japan | 63-169757 |
| Sep. 2, 1988 | [JP] | Japan | 63-123282 |
| Sep. 13, 1988 | [JP] | Japan | 63-229644 |
| Oct. 12, 1988 | [JP] | Japan | 63-257963 |
| Dec. 12, 1988 | [JP] | Japan | 63-314650 |
| Dec. 28, 1988 | [JP] | Japan | 63-170795 |

[51] Int. Cl.$^5$ .................................................. F23G 7/00
[52] U.S. Cl. ...................................... 110/346; 110/237
[58] Field of Search ........................ 110/346, 237, 238

[56] References Cited

U.S. PATENT DOCUMENTS 4,078,914 3/1978 Gold .
4,419,943 12/1983 Faurholdt ........................ 110/237
4,850,290 7/1989 Benoit et al. ..................... 110/346

FOREIGN PATENT DOCUMENTS 2233435 1/1974 Fed. Rep. of Germany .

Primary Examiner—Edward G. Favors
Attorney, Agent, or Firm—Sughrue, Mion, Zinn, Macpeak & Seas

[57] ABSTRACT

A method for disposing of medical waste materials comprises placing waste materials into a container, sealing the container, placing the sealed container into a melting furnace together with metal, and heating the furnace to a temperature sufficient to completely combust or melt the container and the waste materials. An apparatus for disposing of medical waste material has a container with an opening in its top surface and a lid for sealing the container. The container is supported by a support stand including a base, a cover for closing the opening of the container, and a pedal for moving the cover between an open and a closed position.

4 Claims, 3 Drawing Sheets

METHOD FOR DISPOSAL OF MEDICAL WASTE MATERIALS

BACKGROUND OF THE INVENTION

This invention relates to a method for disposing of medical wastes, and particularly to a method which can reliably and safely dispose of medical wastes without it being necessary for humans to contact the wastes. This invention also relates to an apparatus for carrying out this method.

Each day, hospitals, medical clinics, pharmaceutical companies, facilities where medical examinations are performed, and the like (herebelow refferred to collectively as "hospitals" or "a hospital") generate large quantities of medical wastes. Generally, these waste materials are first sorted into groups such as needles, syringes, bottles, and burnable materials. The sorted materials are then rendered harmless by burning, washing, or sterilization as necessary and then disposed of as normal trash. The waste treatment and diposal may be performed by the hospital itself, or it may be performed by a company which is licensed to handle medical wastes. A waste disposal company normally receives waste materials from a hospital in special containers and transports the containers to its place of business. There, the company will remove the medical wastes from the containers, process the wastes in a suitable manner, and then return the containers to the hospital.

During the sorting stage of the above-described conventional processing method for medical wastes, there is a danger of human operators coming into contact with the waste meterials, which creates the possibility of the operators' contacting hepatitis B, AIDS, or other diseases by secondary infection. Waste disposal is also made troublesome by the necessity of separating matallic wastes, such as hypodermic needles, from other waste materials.

There is also the possibility of waste materials such as needles and syringes falling into the hands of drug users or other third parties. As the washing and sterilization of these materials during waste treatment is not complete, such third parties are also subject to secondary infection by dangerous diseases.

Secondary infection by medical wastes is becoming an increasingly serious problem, and there is thus a need for a safe and reliable method for disposing of medical waste materials.

SUMMARY OF THE INVENTION

Accordingly, it is an object of the pressent invention to provide a method and an apparatus for the disposal of medical waste meterials from hospitals which can dispose of these meterials without the need of their being sorted by humans.

It is another object of the present invention to provide a method which can completely destroy sources of secondary infection such as needles and syringes.

It is a further object of the present invention to provide an apparatus for use in carrying out this method.

The present inventors discovered that medical wastes can be safely and efficiently disposed of by charging them little by little into a metal-melting furnace used in the manufacture of steel or the like (sometimes also referred to merely as "metal furnace"). A metal-melting furnace, such as an electric furnace for melting scrap metal in the manufacture of steel, has an extremely high heat capacity. On the average, melting of metal in such a furnace is carried out 20 times per day. Medical wastes can be added to the furnace a little at a time without reducing the ability of the furnace to perform its original purpose of melting metal. The furnace is at a high temperature of 1400 1600 degrees C., so combustible materials in the medical wastes are gasified or converted into slag, while metal items such as needles in the medical wastes are melted and absorbed by the molten steel. Provided that the medical wastes are added in small quantities, they have no adverse effect on refining operations or the quality of the finished steel product resulting from the molten steel in the furnace.

Thus, a waste disposal method in accordance with the present invention comprises the steps of placing medical wastes into a waste storage container, sealing the container, charging the sealed vessel into a metal-melting furnace containing metal, and heating the furnace to a temperature sufficient to combust or melt the container and the waste materials contained inside the container.

A waste disposal apparatus for use in carrying out the method of the present invention has a waste storage container for medical wastes having an opening which can be sealed and a support stand for supporting the container. The support stand includes a base on which a waste storage container can be mounted, a cover which can pivot between an open position and a closed position in which it covers the container, and a mechanism for opening the cover when an operator steps on a pedal In accordance with the method of the present invention, all types of medical wastes can be placed together into the waste storage container without any sorting or sterilization. After being sealed, the container is charged into a metal-melting furnace. The container is sufficiently strong that it can be used for temporary storage of the medical wastes before being placed into the furnace. As no sorting of the waste materials is necessary and as all the waste materials are completely destroyed in the furnace, there is no danger of secondary infection by the waste materials as in conventional disposal methods.

Furthermore, as the support stand is equipped with a cover which can be opened by stepping on a pedal, a person who is disposing of medical wastes does not need to touch the sides of the container or waste materials already inside the container. There is of course no restriction on the type of mechanism used for opening and closing the cover of the container.

After the container is full, it is sealed with a special lid. The container and the lid can be made of any material which is adequately strong and which will burn or melt in a metal furnace. The container should be sturdy enough not to be broken or pierced by sharp items such as hypodermic needles when it is being transported or used for storage. Suitable materials include special types of paper, plastics, and metals.

There are no particular restrictions on the type of melting furnace which can be used to dipose of the medical wastes. Suitable metal-melting furnaces include blast furnaces, top-blown steel-making converters, bottom-blown steel-making converters, top- and bottom-blown steel-making converters, electric furnaces for melting scrap metal (with or without a preheating device for scrap), induction furnaces, high-frequency furnaces, and cupola furnaces.

The disposal method of the present invention can be used to dispose of all types of medical wastes produced by hospitals. A few examples of waste materials which can be disposed of are glass or plastic syringes, metal hypodermic needles, glass, plastic, or metal containers for medicines, test materials, gauze, cotton, bandages, X-ray film, plaster casts, plastic pipes, waste medicines, blood in solid or liquid form, test samples (urine, feces, blood, tissue, etc.), paper diapers, paper, and kitchen refuse.

DESCRIPTION OF THE PREFERRED EMBODIMENTS

Figure 1:
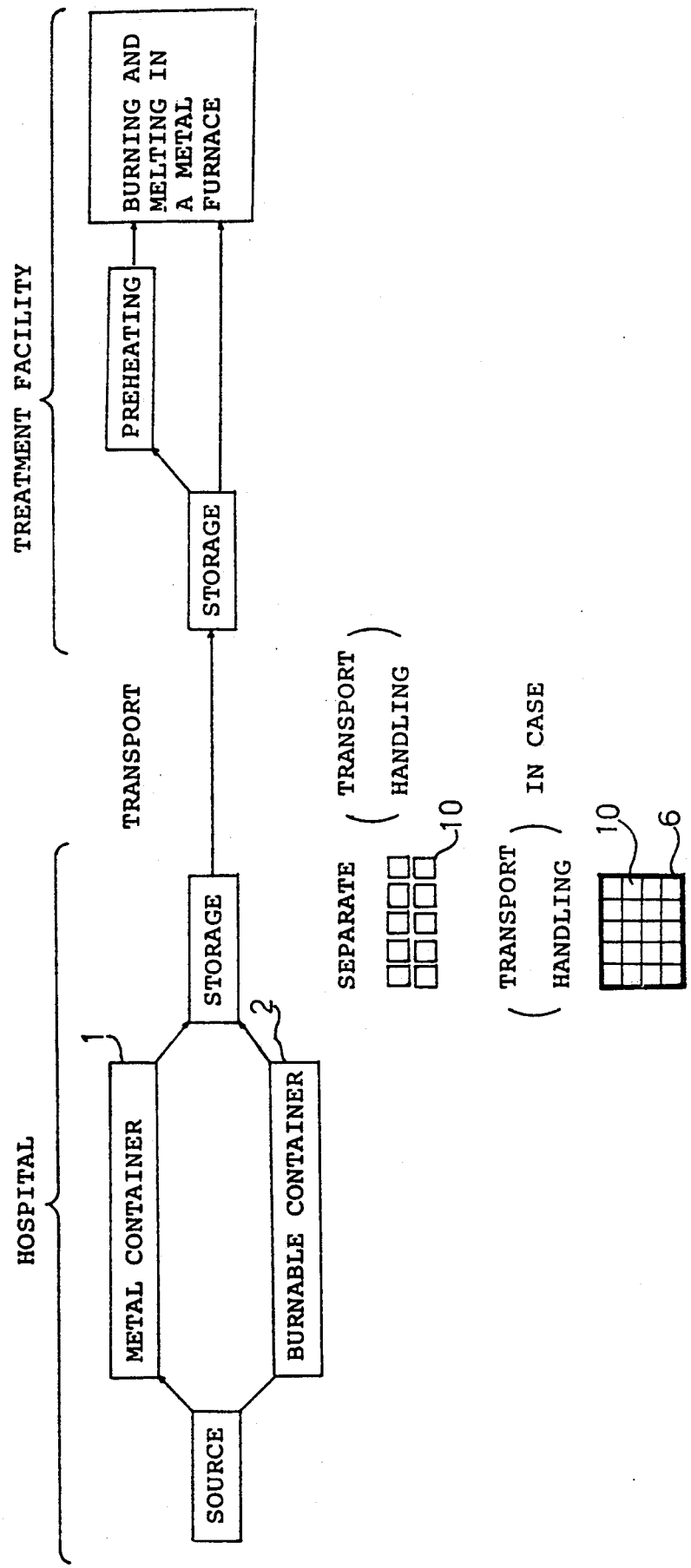
FIG. 1 is a diagram illustrating the step in the method of the present invention.

The method of the present invention will now be described while referring to FIG. 1, which is a diagram illustrating the step of this method.

First, medical waste materials from a source, such as a treatment ward of a hospital, are placed into a waste storage container 1 made of metal or a waste storage container 2 made of a burnable material. When full, the container 1(2) is sealed with a lid. After being temporarily stored, if necessary, the sealed container 10 is transported by vehicle to a disposal facility equipped with a metal-melting furnace.

When a single hospital uses a large number of waste storage containers 10, it is desirable to pack a pluralilty (20, for example) of the filled containers 10 into a special case 6 and then transport the containers 10 inside the case 6 to the disposal facility. The case 6 can be made of metal, plastic, cardboard, or other sturdy material which is formed into a shape such that it can hold a plurality of the waste storage containers 10. Use of a case 6 for transporting the waste storage containers 10 increases the efficiency of transport.

At the disposal facility, the waste storage containers 10 are charged into a metal furnace by means of a crane, a fork lift, or other means which does not require the containers 10 to be touched by humans. Preferably, the case 6 is of a size so that the entire case 6 can be charged into the furnace without removing the containers 10 from the case 6. If necessary, the containers 10 can be subjected to preheating in a separate furnace together with scrap metal to be melted in the metal-melting furnace or metal furnace. If the metal scrap in the preheating stage is heated hot enough, combustible portions of the waste materials can be completely compute in the preheating stage. It is herein to be noted that this embodiment is also within the breadth of the present invention.

A metal-melting furnace is normally heated to a temperature of at least 1400 degrees C. Therefore, both the medical wastes and the waste storage containers 10 are completely burned or melted and rendered entirely harmless.

The waste disposal method of the present invention has the advantage over simple incineration of medical wastes that the temperature of molten metal is much higher than the temperature which can be attained in a typical incinerator, so the waste materials can be completely transformed into harmless substances. Furthermore, whereas an incinerator requires an external source of energy, the amount of excess heat generated by a melting furnace during normal operation is sufficient to dispose of large quantities of medical wastes without an increase in the energy requirements of the melting furnace. Accordingly, disposal of waste materials in a metal-melting furnace is extremely economical from the standpoint of energy consumption.

Next, an apparatus for use in carrying out the method of the present invention will be described. The apparatus includes a waste storage container, illustrated in FIG. 2, and a support stand, illustrated in FIG. 4, for supporting the container.

Figure 2:
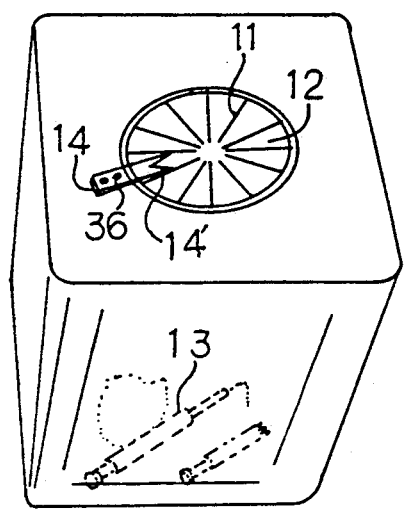
FIG. 2 is a perspective view of a waste storage container for use in the method of the present invention.

As shown in FIG. 2, the waste storage container 10 is a box-shaped container having an opening 12 in its top surface. A plurality of pins 11 are embedded in the periphery of the opening 12. The pins 11 extend downwards and towards the center of the opening 12 so as to collectively describe the shape of a funnel. The space between the inner ends of the pins 11 at the center of the opening 12 is preferably small enough to prevent a person from inserting his hand into the container 10. These downward-extendidng pins 11 prevent waste materials from being easily removed from the container 10 once they are thrown into it. As long as the pins 11 are able to accomplish this purpose, there are no restrictions on their shape, the material of which they are made, or the manner of installation. Instead of pins, piano wire, reinforced plastic wire, or petal-shaped members can be employed.

A needle puller 14 is secured to the top of the container 10 in a suitable location by screws 36 or the like. The needle puller 14 is made from a metal plate which extends into the opening 12 of the container 10 and which has a notch 14' formed in its end. A hypodermic needle can be removed from a syringe by means of the notch 14' in the needle puller 14.

Figure 3:
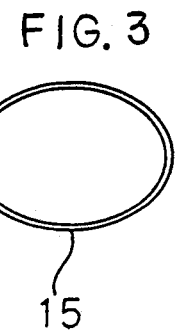
FIG. 3 is a plan view of a lid for sealing the container of FIG. 2.

When the container 10 becomes full of medical waste materials 13, it is sealed with a special lid 15, illustrated in FIG. 3, and then temporarily stored.

Figure 4:
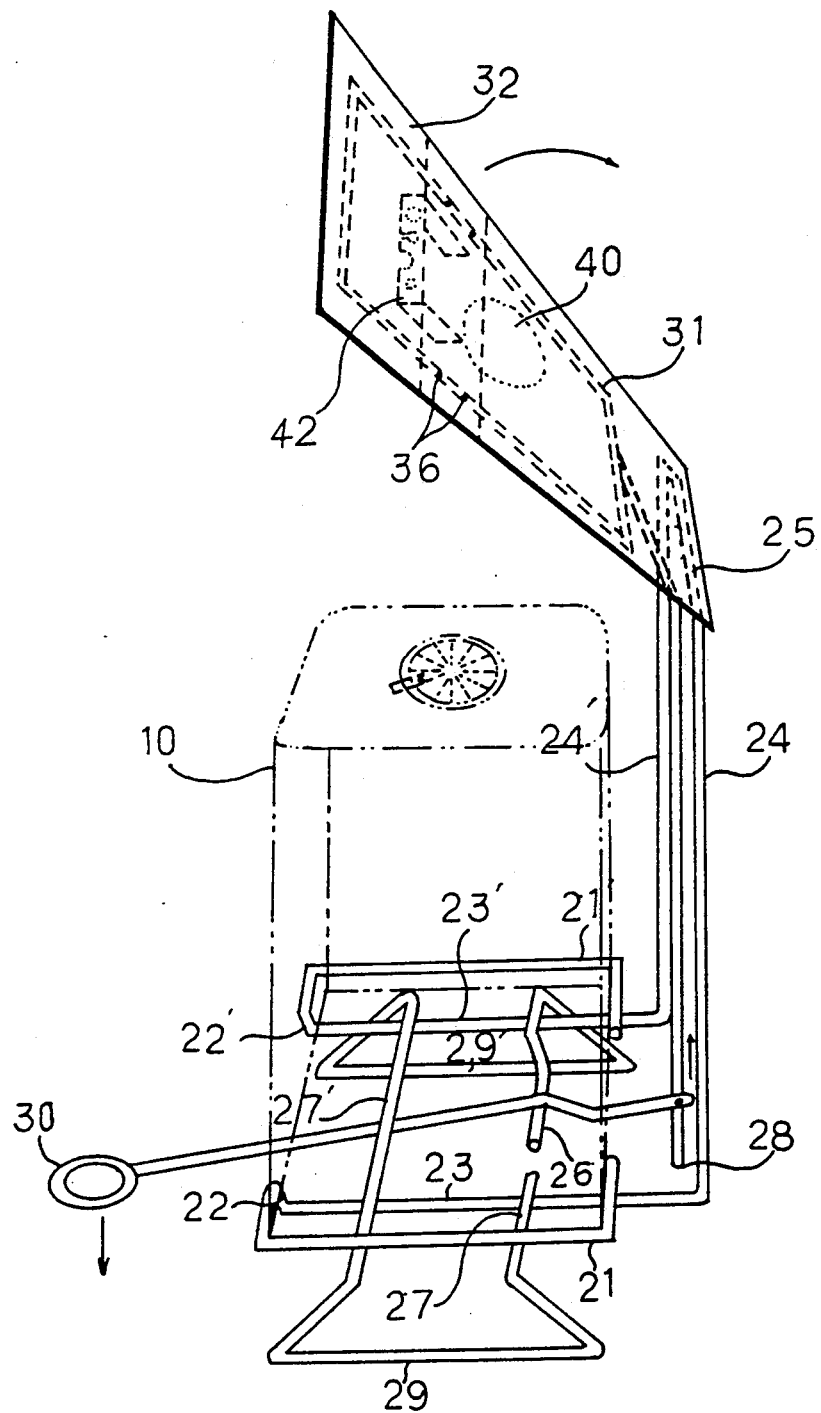
FIG. 4 is a perspective view of a support stand for supporting the container of FIG. 2.

FIG. 4 illustrates an example of a container support stand for supporting a waste storage container 10 during use. For lightness, the illustrated example is made from metal pipes, but there are no restrictions on the materials which can be used.

A first pipe is bent into the shape of a base 29 having two straight sections which lie on a flat surface such as a floor, and two horizontal sections 27 and 27' on which the container 10 is placed. A second pipe is bent so as to form two horizontal sections 21 and 21', two short vertical sections 22 and 22' which adjoin horizontal sections 21 and 21', two horizontal sections 23 and 23' which adjoin the vertical sections 21 and 21', and extend parallel to horizontal sections 21 and 21', two long vertical sections 24 and 24' which extend for the height of a container 10, and a horizontal section 25 which connects the upper ends of vertical sections 24 and 24'. Horizontal sections 23 and 23' are secured to the top of the base 29. Horizontal sections 21 and 21' and vertical sections 22 and 22' are shaped so as to support the bottom portion of a container 10 placed on the horizontal sections 27, 27' of the base 29.

A cover for the container 10 is pivotably mounted on the top of the support stand. The cover comprises a rectangular frame 31 and a plate 32 which is secured to the frame 31 by screws 36 or other suitable means. The plate 32 is rotatably connected to horizontal section 25 of the second pipe. A seal 40 made of a suitable resillient material such as foam rubber is secured to the underside of the plate 32. When the cover is in a closed position, the seal 40 fits over the opening 12 of a container 10 and prevents odors from escaping from the container 10.

The cover of the container 10 is normally pivoted by gravity to a closed position. The cover can be swung to an open position by means of a lever 30 having a crook at one end which serves as a foot pedal. The lever 30 rests on the upper portion of the base 29, which serves as a fulcrum for the lever 30. The end of the lever 30 opposite the pedal is rotatably connected to the lower end of a vertical connecting rod 28. The upper end of the connecting rod 28 is bent towards in the lengthwise direction of the cover and is secured to a cross piece of the frame 31. When a person steps on the pedal 30, the right end of the lever 30 in FIG. 4 pivots upwards, forcing the connecting rod 28 upwards The upward movement of the connecting rod 28 causes the cover to swing clockwise in FIG. 4 to an open position as shown by the arrow. When the lever 30 is released, the cover swings back to a closed position in which it seals the container 10.

A container 10 can be easily mounted atop the support stand. When it becomes full, the container 10 is removed from the support stand and replaced with an empty container 10.

A syringe breaking mechanism 42 is mounted on the underside of the cover of the support stand.

Figure 5:
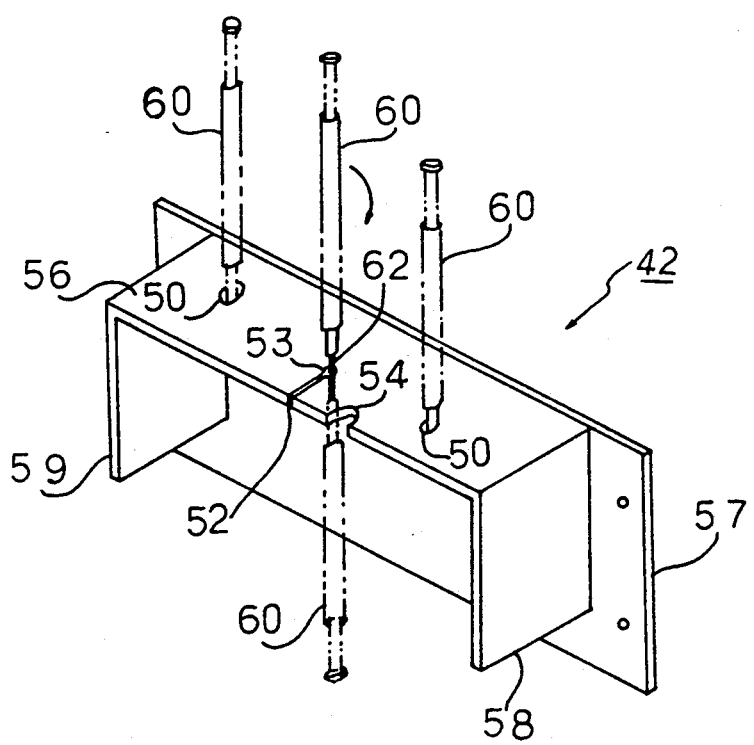
FIG. 5 is a perspective view of a device for breaking hypodermic syringes which is mounted on the inside of the cover of the support stand.

As shown in FIG. 5, the syringe breaking mechanism 42 includes a plate 57 which is secured to the cover by screws, and two side plates 58, 59 and a top plate 56 which are secured to plate 57 and extend upwards therefrom. The top plate 56 has a number of through holes 50 formed therein. In order to destroy a syringe 60, the tip or the body of the syringe 60 is inserted into one of the holes 50 and the syringe is then twisted sideways as shown by the arrow in FIG. 5, thus breaking the syringe and making it unusable. A slit 52 having the shape of a key hole is formed in an edge of the top plate 56. If a hypodermic needle is inserted into this slit 52 and then the syringe 60 to which the needle is connected is pivoted sideways, the needle will be bent and rendered unusable. The side plates 58, 59 prevent pieces of glass or plastic from being scattered when a syringe is broken. After a syringe is broken by this mechanism, it is discarded in the waste storage container 10. The syringe breaking mechanism 42 can be installed at locations other than the inner surface of the cover, but this location is particularly suitable since broken glass will tend to fall directly into the container 10 which is disposed beneath the breaking mechanism 42.

Next, several working examples of the method of the present invention will be described.

EXAMPLE 1

Plastic waste storage containers measuring 30 cm square and 40 cm high and having a wall thickness of 2 mm were mounted on support stands like the one illustrated in FIG. 4 and then placed in a number of hospitals. Medical waste materials were discarded into the waste storage containers without being sorted. When the containers were full, they were sealed with a lid, removed from the support stands, and then stored.

The sealed containers were loaded on a special truck using a fork-lift or the like without being touched by human hands and then transported to a treatment facility, where they were stored in a sealed state. Then, using a fork-lift, twenty containers at a time were placed into a clamshell-type charging bucket together with scrap metal. The scrap metal and the containers where together subjected to refining at above 1600 degrees C. in a 70-ton electric furnace. The plastic waste storage containers and the medical wastes contained therein, including needles, were completely combusted or melted in the furnace.

The molten steel was sampled at the time of tapping. The amount of medical wastes present in the molten steel was less than 0.5% and had no effect on the molten steel or on the quality of the finished product which was manufactured from the molten steel.

EXAMPLE 2

The procedure of Example 1 was repeated using steel waste storage containers measuring 30 cm in diameter and 36 cm in height and having a wall thickness of 0.4 mm. The steel containers and the waste materials contained therein were completely combusted or melted in a 50-ton electric furnace together with scrap metal. As in Example 1, the waste materials had no significant effect on the molten steel.

What is claimed is:

1. A method for disposing of medical waste materials comprising the steps of:
    placing medical waste materials into a container;
    sealing the container;
    placing the sealed container into a metal-melting furnace together with metal; and
    heating the furnace to a temperature sufficient to completely combust or melt the container and the medical waste materials.

2. A method as claimed in claim 1 wherein said container is made of metal.

3. A method as claimed in claim 1 wherein said container is made of plastic.

4. A method as claimed in claim 1 wherein said metal-melting furnace is an electric furnace for melting scrap metal.

* * * * *